United States Patent [19]

Evans et al.

[11] Patent Number: 4,555,509
[45] Date of Patent: * Nov. 26, 1985

[54] ANTI-HYPERTENSIVE BENZO[B]PYRAN-3-OLS

[75] Inventors: John M. Evans, Roydon; Robin E. Buckingham, Welwyn Garden City; Kenneth Willcocks, Harlow, all of England

[73] Assignee: Beecham Group p.l.c., England

[*] Notice: The portion of the term of this patent subsequent to Apr. 9, 2002 has been disclaimed.

[21] Appl. No.: 592,117

[22] Filed: Mar. 22, 1984

[30] Foreign Application Priority Data

Mar. 24, 1983 [GB] United Kingdom ............... 8308063

[51] Int. Cl.[4] ............... A61K 31/445; A61K 31/40; C07D 405/04
[52] U.S. Cl. ............... 514/278; 514/320; 514/409; 514/422; 546/15; 546/196; 548/407; 548/525; 549/345; 549/399
[58] Field of Search ............... 546/196, 15; 548/525, 548/407; 549/345, 399; 424/267, 274; 514/278, 320, 409, 422

[56] References Cited

U.S. PATENT DOCUMENTS

| 4,238,501 | 12/1980 | Kabbe et al. | 424/283 |
|---|---|---|---|
| 4,251,537 | 2/1981 | Evans | 424/267 |
| 4,363,811 | 12/1982 | Evans et al. | 548/525 |
| 4,366,163 | 12/1982 | Evans et al. | 546/196 |
| 4,446,113 | 5/1984 | Evans et al. | 424/267 |
| 4,510,152 | 4/1985 | Faruk | 546/196 X |

FOREIGN PATENT DOCUMENTS

| 0009912 | 4/1980 | European Pat. Off. | 548/525 |
|---|---|---|---|
| 0028064 | 5/1981 | European Pat. Off. | 546/196 |
| 0033612 | 8/1981 | European Pat. Off. | 546/199 |
| 46652 | 3/1982 | European Pat. Off. | 549/399 |
| 2468601 | 5/1981 | France | 546/196 |
| 1548222 | 7/1979 | United Kingdom | 546/196 |

OTHER PUBLICATIONS

Lap, A., et al., *Aust. J. Chem.*, 1979, 32, pp. 619–636.

Primary Examiner—Richard A. Schwartz
Attorney, Agent, or Firm—Jacobs & Jacobs

[57] ABSTRACT

Compounds of the formula (I):

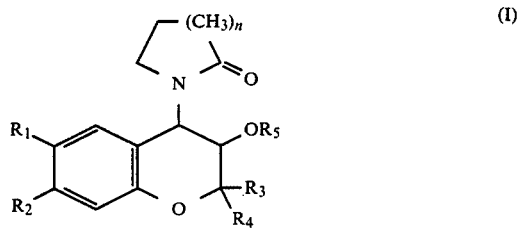

wherein:
one of $R_1$ and $R_2$ is hydrogen and the other is $C_{1-6}$ alkylthiocarbonyl, $C_{1-6}$ alkoxy thiocarbonyl, $C_{1-6}$ alkyl-thiocarbonyloxy, 1-mercapto $C_{2-7}$ alkyl or formyl;
one of $R_3$ and $R_4$ is hydrogen or $C_{1-4}$ alkyl and the other is $C_{1-4}$ alkyl, or $R_3$ and $R_4$ together with the carbon atom to which they are attached are $C_{3-6}$ spiroalkyl;
$R_5$ is hydrogen, $C_{1-3}$ alkyl or $C_{1-8}$ acyl; and
n is 1 or 2; the lactam group being trans to the $OR_5$ group, having anti-hypertensive activity.

11 Claims, No Drawings

ANTI-HYPERTENSIVE BENZO[B]PYRAN-3-OLS

The present invention relates to novel benzopyrans having pharmacological activity, to processes and intermediates for use in their preparation, and to their use in the treatment of mammals.

U.S. Pat. Nos. 4,110,347, 4,251,537 and European Patent Publication No. 9912 disclose 3,4-dihydro-4H-benzopyrans that are described as having anti-hypertensive activity.

A further class of structurally distinct 3,4-dihydro-4H-benzopyrans has now been discovered which, moreover, have been found to have blood pressure lowering activity.

Accordingly the present invention provides a compound of formula (I):

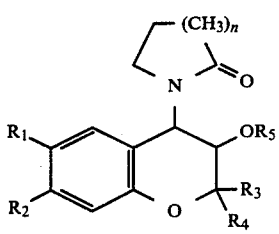

wherein:
one of $R_1$ and $R_2$ is hydrogen and the other is $C_{1-6}$ alkyl-thiocarbonyl, $C_{1-6}$ alkoxy-thiocarbonyl, $C_{1-6}$ alkyl-thiocarbonyloxy, 1-mercapto $C_{2-7}$ alkyl or formyl;

one of $R_3$ and $R_4$ is hydrogen or $C_{1-4}$ alkyl and the other is $C_{1-4}$ alkyl, or $R_3$ and $R_4$ together with the carbon atom to which they are attached are $C_{3-6}$ spiroalkyl;

$R_5$ is hydrogen, $C_{1-3}$ alkyl or $C_{1-8}$ acyl; and n is 1 or 2; the lactam group being trans to the $OR_5$ group.

The other of $R_1$ and $R_2$, when one of them is hydrogen, is preferably, $C_{1-6}$ alkyl-thiocarbonyl, $C_{1-6}$ alkoxy-thiocarbonyl or formyl, in particular $C_{1-6}$ alkyl-thiocarbonyl or formyl.

The alkyl moieties of alkyl-containing groups, in respect of the other of $R_1$ and $R_2$, are preferably methyl or ethyl.

Preferably, $R_2$ is hydrogen and $R_1$ is as defined hereinbefore for the other of $R_1$ and $R_2$.

Preferably, $R_3$ and $R_4$ are both $C_{1-4}$ alkyl, in particular, both methyl or ethyl, preferably both methyl.

When $R_5$ is alkyl, preferred examples thereof include methyl and ethyl, of which methyl is more preferred. When $R_5$ is acyl, a preferred class is unsubstituted carboxylic acyl, such as aliphatic acyl or benzoyl. However, $R_5$ is preferably hydrogen.

The compounds of formula (I) cover both a piperidone substituent (when n=2) and a pyrrolidone substituent (when n=1).

It is preferred that the compounds of formula (I) are in substantially pure form.

The compounds of formula (I) are asymmetric and, therefore, exist in optically active forms. The present invention extends to all such forms individually and to mixtures of them.

The present invention also provides a process for the preparation of a compound of formula (I), which comprises cyclising a compound of formula (II), or a metal salt thereof:

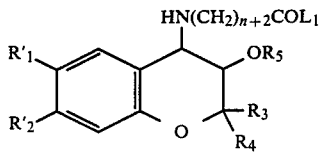

wherein one of $R_1'$ and $R_2'$ is hydrogen or a group or atom convertible into hydrogen and the other is $C_{1-6}$ alkyl-thiocarbonyl, $C_{1-6}$ alkoxy-thiocarbonyl, $C_{1-6}$ alkyl-thiocarbonyloxy, 1-mercapto $C_{2-7}$ alkyl, formyl or a group or atom convertible thereto, $R_3$ to $R_5$ and n are as defined hereinbefore, and $L_1$ is a leaving group; the substituted amino group being trans to the $OR_5$ group; in the case when one of $R_1'$ and $R_2'$ is a group or atom convertible into hydrogen, converting the group or atom into hydrogen; in the case when the other of $R_1'$ and $R_2'$ is a group or atom convertible into $C_{1-6}$ alkyl-thiocarbonyl, $C_{1-6}$ alkoxy-thiocarbonyl, $C_{1-6}$ alkyl-thiocarbonyloxy, 1-mercapto $C_{2-7}$ alkyl or formyl, converting the group or atom into $C_{1-6}$ alkyl-thiocarbonyl, $C_{1-6}$ alkoxy-thiocarbonyl, $C_{1-6}$ alkyl-thiocarbonyloxy, 1-mercapto $C_{2-7}$ alkyl or formyl; and optionally converting $R_1$, $R_2$ or $R_5$ in the resulting compound of formula (I) into another $R_1$, $R_2$ or $R_5$, as defined hereinbefore.

The leaving group ($L_1$) is a group that is displaceable by a secondary amino nucleophile. Preferred examples of such groups include hydroxy and, in particular, $C_{1-4}$ alkoxy, such as ethoxy.

The cyclisation is normally carried out by heating the compound of formula (II) under reflux in an inert solvent, such as xylene or toluene.

When a metal salt of formula (II) is used, the sodium salt is preferred. However, it is even more preferred not to use a metal salt at all, especially as any elimination side reactions are thereby avoided.

Examples of a conversion of a group or atom into hydrogen or into $C_{1-6}$ alkyl-thiocarbonyl, $C_{1-6}$ alkoxy-thiocarbonyl, $C_{1-6}$ alkyl-thiocarbonyloxy, 1-mercapto $C_{2-7}$ alkyl or formyl are generally known in the art.

Examples of optional conversions of $R_5$ in the compound of formula (I) into another $R_5$, as defined hereinbefore, are also generally known in the art. For example, when $R_5$ is hydrogen, the hydroxy group may be alkylated using an alkyl iodide, the reaction being carried out in an inert solvent, such as toluene, in the presence of a base, such as potassium t-butoxide. Alternatively, the hydroxy group may be acylated using a carboxylic acid or derivative thereof, such as an anhydride, the reaction being carried out in a non-hydroxylic solvent in the presence of a condensation promoting agent, such as dicyclohexylcarbodiimide.

A compound of formula (II) may be prepared by reacting a compound of formula (III):

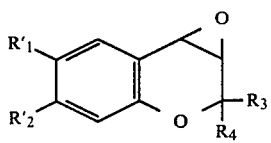

wherein $R_1'$ and $R_2'$ and $R_3$ and $R_4$ are as defined hereinbefore, with a compound of formula (IV):

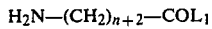

wherein n and $L_1$ are as defined hereinbefore; and optionally converting $R_5$ in the resulting compound of formula (II) into another $R_5$, as defined hereinbefore.

The reaction is normally carried out in a solvent at low, medium or high temperature. The solvent may be an alcohol, such as methanol or ethanol.

When $L_1$ is hydroxy the reaction proceeds well if carried out in refluxing ethanol in the presence of aqueous sodium carbonate. When $L_1$ is $C_{1-4}$ alkoxy, the reaction is preferably carried out in the presence of sodium hydroxide in ethanol.

The optional conversion of $R_5$, which is hydrogen, in the resulting compound of formula (II) into another $R_5$, as defined hereinbefore, may be carried out as described hereinbefore.

Under some conditions, the resulting compound of formula (II) may spontaneously cyclise to form a compound of formula (I).

A compound of formula (III) may be prepared, preferably in situ, by reacting a compound of formula (V):

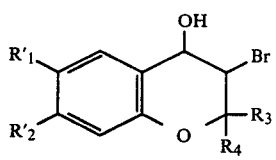

(V)

wherein $R_1'$, $R_2'$, $R_3$ and $R_4$ are as defined hereinbefore; the hydroxy group being trans to the bromo atom; with a base, such as potassium hydroxide, in ether or aqueous dioxan.

Alternatively, a compound of formula (II) may be prepared by reacting a compound of formula (VI):

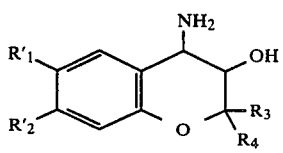

(VI)

wherein $R_1'$, $R_2'$, $R_3$ and $R_4$ are as defined hereinbefore; the amino group being trans to the hydroxy group; with a compound of formula (VII):

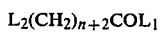

$L_2(CH_2)_{n+2}COL_1$ (VII)

wherein n and $L_1$ are as defined hereinbefore and $L_2$ is a leaving group.

The leaving group ($L_2$) is a group that is displaceable by a primary amino nucleophile. Preferred examples of such groups include halo, such as chloro and bromo.

A compound of formula (VI) may be prepared by a reaction of a compound of formula (III) with ethanolic ammonium hydroxide solution. Alternatively, it may be prepared by reduction with zinc and hydrochloric acid of a compound of formula (VIII):

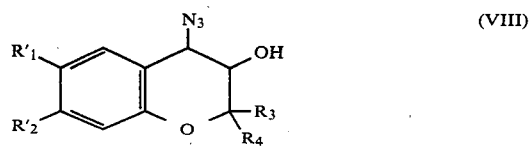

(VIII)

wherein $R_1'$, $R_2'$, $R_3$ and $R_4$ are as defined hereinbefore; the azide group being trans to the hydroxy group.

A compound of formula (VIII) may in turn be prepared from a compound of formula (III) by reaction with sodium azide in the presence of boric acid in for example dimethylformamide.

Alternatively, a compound of formula (I) may be prepared by oxidising a compound of formula (IX), or a metal salt thereof:

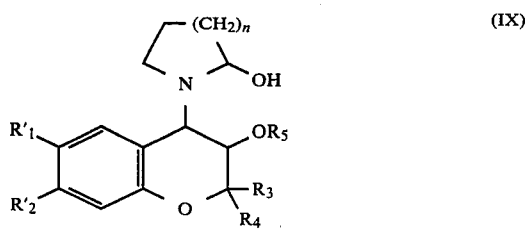

(IX)

wherein $R_1'$, $R_2'$, $R_3$ to $R_5$ and n are as defined hereinbefore; the nitrogen-containing group being trans to the $OR_5$ group; in the case when one of $R_1'$ and $R_2'$ is a group or atom convertible into hydrogen, converting the group or atom into hydrogen; in the case when the other of $R_1'$ and $R_2'$ is a group or atom convertible into $C_{1-6}$ alkyl-thiocarbonyl, $C_{1-6}$ alkoxy-thiocarbonyl, $C_{1-6}$ alkyl-thiocarbonyloxy, 1-mercapto $C_{2-7}$ alkyl or formyl, converting the group or atom into $C_{1-6}$ alkyl-thiocarbonyl, $C_{1-6}$ alkoxy-thiocarbonyl, $C_{1-6}$ alkyl-thiocarbonyloxy, 1-mercapto $C_{2-7}$ alkyl or formyl; and optionally converting $R_1$, $R_2$ or $R_5$ in the resulting compound of formula (I) into another $R_1$, $R_2$ or $R_5$, as defined hereinbefore.

The oxidation is preferably carried out in a solvent such as aqueous methanol with a metal periodate such as potassium periodate.

A compound of formula (IX) may be prepared by cyclising, in the presence of an acid, a compound of formula (X):

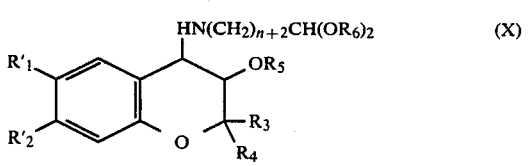

(X)

wherein $R_1'$, $R_2'$, $R_3$ to $R_5$ and n are as defined hereinbefore and $R_6$ is $C_{1-4}$ alkyl; the substituted amino group being trans to the $OR_5$ group.

A compound of formula (X) may in turn be prepared by reacting a compound of formula (III), as defined hereinbefore, with a compound of formula (XI):

$H_2N(CH_2)_{n+2}CH(OR_6)_2$ (XI)

wherein $R_6$ and n are as defined hereinbefore.

As a further alternative, a compound of formula (I) may be prepared by reacting a compound of formula (III), as defined hereinbefore, with an anion of formula (XII):

wherein n is as defined hereinbefore; in the case when one of $R_1'$ and $R_2'$ is a group or atom convertible into hydrogen, converting the group or atom into hydrogen; in the case when the other of $R_1'$ and $R_2'$ is a group or atom convertible into $C_{1-6}$ alkyl-thiocarbonyl, $C_{1-6}$ alkoxy-thiocarbonyl, $C_{1-6}$ alkyl-thiocarbonyloxy, 1-mercapto $C_{2-7}$ alkyl or formyl, converting the group or atom into $C_{1-6}$ alkyl-thiocarbonyl, $C_{1-6}$ alkoxy-thiocarbonyl, $C_{1-6}$ alkyl-thiocarbonyloxy, 1-mercapto $C_{2-7}$ alkyl or formyl; and optionally converting $R_1$, $R_2$ or $R_5$ in the resulting compound of formula (I) into another $R_1$, $R_2$ or $R_5$, as defined hereinbefore.

The reaction is, preferably, carried out in a solvent, such as dimethylsulphoxide, in the presence of a base, such as sodium hydride.

A compound of formula (III) may be prepared in situ from the corresponding compound of formula (V). In such circumstances, it is advantageous not to add the lactam, which forms the anion of formula (XII), until sufficient time has elapsed for the epoxide of formula (III) to be produced.

As a yet further alternative, a compound of formula (I) may be prepared by cyclising a compound of formula (XIII):

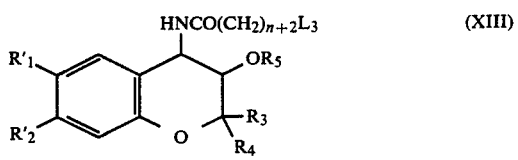

wherein $R_1'$, $R_2'$, $R_3$ to $R_5$ and n are as defined hereinbefore and $L_3$ is a leaving group; the substituted amino group being trans to the $OR_5$ group; in the case when one of $R_1'$ and $R_2'$ is a group or atom convertible into hydrogen, converting the group or atom into hydrogen; in the case when the other of $R_1'$ and $R_2'$ is a group or atom convertible into $C_{1-6}$ alkyl-thiocarbonyl, $C_{1-6}$ alkoxy-thiocarbonyl, $C_{1-6}$ alkyl-thiocarbonyloxy, 1-mercapto $C_{2-7}$ alkyl or formyl, converting the group or atom into $C_{1-6}$ alkyl-thiocarbonyl, $C_{1-6}$ alkoxy-thiocarbonyl, $C_{1-6}$ alkyl-thiocarbonyloxy, 1-mercapto $C_{2-7}$ alkyl or formyl; and optionally converting $R_1$, $R_2$ or $R_5$ in the resulting compound of formula (I) into another $R_1$, $R_2$ or $R_5$, as defined hereinbefore.

The leaving group ($L_3$) is a group that is displaceable by a secondary amino nucleophile adjacent to a carbonyl function. A preferred example is chloro.

The cyclisation reaction is preferably carried out in a solvent such as dimethylformamide in the presence of a base, such as sodium hydride.

A compound of formula (XIII) may be prepared by reacting a compound of formula (VI) with a compound of formula (XIV):

$$L_3(CH_2)_{n+2}COL_4 \quad (XIV)$$

wherein $L_3$ and n are as defined hereinbefore and $L_4$ is a leaving group.

The leaving group ($L_4$) is a group that, when adjacent a carbonyl function, is displaceable by a primary amino nucleophile.

The reaction is preferably carried out in a solvent, such as chloroform or methylene chloride, in the presence of aqueous base, such as aqueous sodium hydroxide.

In the reactions with the epoxide of formula (III), the trans isomer is specifically formed.

Compounds of formula (V) are known and may be prepared in accordance with any appropriate known process, for example, by the process described in the aforementioned U.S. patents and European patent publications. Schematically, such process can be depicted thus:

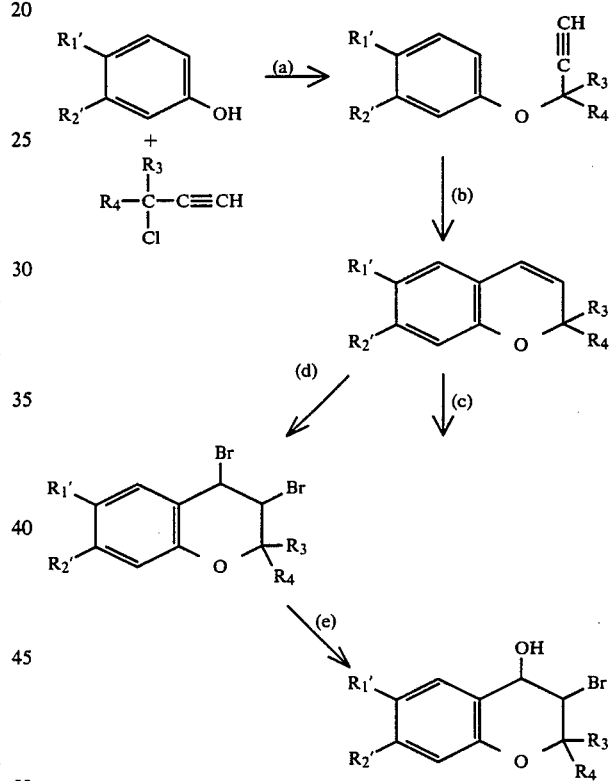

(a) Room temperature; NaOH/40% benzyltrimethylammonium hydroxide in methanol;
(b) Heat in o-dichlorobenzene;
(c) N—bromosuccinimide/dimethylsulphoxide/water;
(d) Bromine in carbon tetrachloride; and
(e) Acetone/water.

The above process may produce mixtures of compounds during reaction (b) owing to the two sites available for ring formation. It is therefore advisable to remove any of the undesired compound by, for example, chromatography, before reaction (c) or (d).

Instead of carrying out the conversion of a group or atom into hydrogen or group or atom into one of the class of subsituents defined hereinbefore for the other of $R_1$ and $R_2$ after cyclising a compound of formula (II) or (XIII), or after oxidising a compound of formula (IX), or after reacting a compound of formula (III) with an anion of formula (XII), it is generally preferred that any such conversions are carried out at an earlier stage preferably on the chromene produced after reaction (b) above.

As mentioned previously, the compounds of formula (I) exist in optically active forms, and the processes of the present invention produce mixtures of such forms. The individual isomers may be separated one from another by chromatography using a chiral phase.

It is preferred that the compounds of formula (I) are isolated in substantially pure form.

The intermediates of (II), (III), (V), (VI), (VIII), (IX) (X) and (XIII) are novel and constitute part of the invention. Collectively, they are of formula (XV):

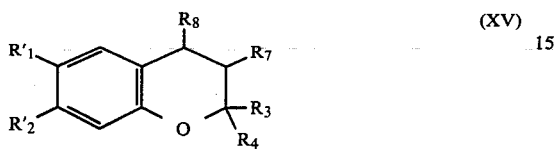

wherein $R_1'$, $R_2'$, $R_3$ and $R_4$ are as defined hereinbefore and $R_7$ is $OR_5$, in which $R_5$ is as defined hereinbefore, and $R_8$ is $-HN(CH_2)_{n+2}COL_1$, $-NH_2$, $-N_3$,

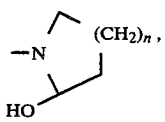

$-HN(CH_2)_{n+2}CH(OR_6)_2$ or $-HNCO(CH_2)_{n+2}L_3$, in which n, $L_1$, $L_3$ and $R_6$ are as defined hereinbefore, or $R_7$ is bromo and $R_8$ is hydroxy, or $R_7$ and $R_8$ together are oxygen; $R_7$, when $OR_5$ or bromo, being trans to $R_8$.

Preferably, $R_1'$ and $R_2'$ in a compound of formula (XV) are $R_1$ and $R_2$ as defined hereinbefore.

As mentioned previously, the compounds of formula (I) have been found to have blood-pressure lowering activity. They are therefore useful in the treatment of hypertension.

The present invention, accordingly, provides a pharmaceutical composition which comprises a compound of this invention and a pharmaceutically acceptable carrier. In particular, the present invention provides an anti-hypertensive pharmaceutical composition which comprises an anti-hypertensive effective amount of a compound of this invention and a pharmaceutically acceptable carrier.

The compositions are preferably adapted for oral administration. However, they may be adapted for other modes of administration, for example parenteral administration for patients suffering from heart failure.

In order to obtain consistency of administration it is preferred that a composition of the invention is in the form of a unit-dose. Suitable unit dose forms include tablets, capsules and powders in sachets or vials. Such unit dose forms may contain from 1 to 100 mg of a compound of the invention and more usually from 2 to 50 mg, for example 5 to 25 mg such as 6, 10, 15 or 20 mg. Such compositions may be administered from 1 to 6 times a day, more usually from 2 to 4 times a day, in a manner such that the daily dose is from 5 to 200 mg for a 70 kg human adult and more particularly from 10 to 100 mg.

The compositions of the invention may be formulated with conventional excipients, such as a filler, a disintegrating agent, a binder, a lubricant, a flavouring agent and the like. They are formulated in conventional manner, for example in a manner similar to that used for known anti-hypertensive agents, diuretics and β-blocking agents.

The present invention further provides a compound of formula (I) for use in the treatment of hypertension.

The present invention yet further provides a method of treating hypertension in mammals including man, which comprises administering to the suffering mammal an anti-hypertensive effective amount of a compound of formula (I) or a pharmaceutical composition of the invention.

The following examples relate to the preparation of a compound of formula (I).

EXAMPLE 1

3,4-Dihydro-2,2-dimethyl-6-formyl-trans-4-(2-oxo-1-pyrroli-dinyl)-2H-benzo[b]pyran-3-ol

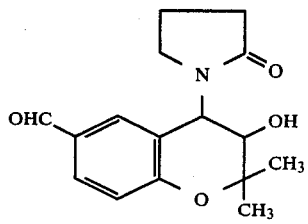

To a solution of 3,4-dihydro-2,2-dimethyl-3,4-epoxy-6-formyl-2H-benzo[b]pyran (0.48 g, prepared using the method described in U.K. Pat. No. 1.511.187) and 2-pyrrolidone (0.20 g) in dry dimethyl sulphoxide (30 ml) was added sodium hydride (0.07 g, 80% dispersion in oil). After stirring at room temperature for 4 hours, water was added and the aqueous phase immediately extracted with ethyl acetate. The organic layer was washed with water and brine and dried over magnesium sulphate. Filtration, evaporation and chromatography (chromatotron, pentane-ethyl acetate gradient elution, 2 mm silica gel) gave a fraction (150 mgs) which was recrystallised to give the title compound as crystals (80 mgs) of m.p. 196°–197.5° C.

NMR (CDCl$_3$+D$_2$O)δ 1.32 (3H, s); 1.56 (3H, s); 1.80–2.30 (2H, m); 2.40–2.75 (2H, m); 2.90–3.50 (2H, m); 3.76 (1H, d, J=10Hz); 5.33 (1H, d, J=10Hz); 6.96 (1H, d, J=9Hz); 7.45–7.55 (1H, m); 7.74 (1H, g, J=9,2Hz); 9.87 (1H, s).

3,4-Dihydro-2,2-dimethyl-6-formyl-trans-4-(2-oxo-1-piperidinyl)-2H-benzol[b]pyran-3-ol is prepared in a similar manner.

EXAMPLE 2

6-Thioacetyl-3,4-dihydro-2,2-dimethyl-trans-4-(2-oxo-1-pyrrolidinyl)-2H-benzo[b]pyran-3-ol

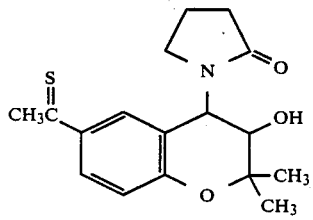

The title compound is prepared by reaction between 6-thioacetyl-3,4-dihydro-2,2-dimethyl-3,4-epoxy-2H- benzo[b]pyran and 2-pyrrolidone in dimethylsulphoxide in the presence of sodium hydride.

6-Thioacetyl-3,4-dihydro-2,2-dimethyl-trans-4-(2-oxo-1-piperidinyl)-2H-benzo[b]pyran-3-ol is prepared in a similar manner.

EXAMPLE 3

6-Methoxy-thiocarbonyl-3,4-dihydro-2,2-dimethyl-trans-4-(2-oxo-1-pyrrolidinyl)-2H-benzo[b]pyran-3-ol

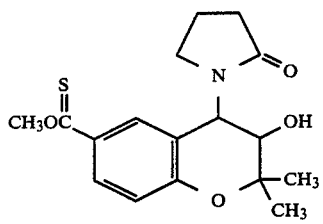

The title compound is prepared by reaction between 6-methoxy-thiocarbonyl-3,4-dihydro-2,2-dimethyl-3,4-epoxy-2H-benzo[b]pyran and 2-pyrrolidone in dimethylsulphoxide in the presence of sodium hydride.

6-Methoxy-thiocarbonyl-3,4-dihydro-2,2-dimethyl-trans-4-(2-oxo-1-piperidinyl)-2H-benzo[b]pyran-3-ol is prepared in a similar manner.

PHARMACOLOGICAL DATA

Systolic blood pressures were recorded by a modification of the tail cuff method described by I. M. Claxton, M. G. Palfreyman, R. H. Poyser, R. L. Whiting, European Journal of Pharmacology, 37, 179 (1976). A W+W BP recorder, model 8005, was used to display pulses. Prior to all measurements rats were placed in a heated environment (33.5±0.5° C.) before transfer to a restraining cage. Each determination of blood pressure was the mean of at least 6 readings. Spontaneously hypertensive rats (ages 12–18 weeks) with systolic blood pressures >170 mmHg were considered hypertensive.

| Compound of Example 1 | Time Post Dose Hours | % Change in Systolic Blood Blood | % Change in Heart Rate |
|---|---|---|---|
| 5 rats | | | |
| Dose 10 mg/kg | 1 | −20 ± 10* | −3 ± 2 |
| p.o. | 2 | −25 ± 6** | −5 ± 2 |
| Initial Blood | 4 | −20 ± 5 | −10 ± 3 |
| Pressure | 6 | −7 ± 5 | −11 ± 2 |
| 218 ± 6 mmHg | | | |
| Initial Heart Rate | | | |
| 481 ± 15 beats/min | | | |

*1 rat had no measurable pulse
**1 rat dead

What we claim is:
1. A compound of formula (I):

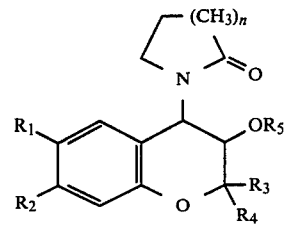

wherein:
one of $R_1$ and $R_2$ is hydrogen and the other is $C_{1-6}$ alkyl-thiocarbonyl, $C_{1-6}$ alkoxy-thiocarbonyl, $C_{1-6}$ alkyl-thiocarbonyloxy, 1-mercapto $C_{2-7}$ alkyl or formyl;
one of $R_3$ and $R_4$ is hydrogen or $C_{1-4}$ alkyl and the other is $C_{1-4}$ alkyl, or $R_3$ and $R_4$ together with the carbon atom to which they are attached are $C_{3-6}$ spiroalkyl;
$R_5$ is hydrogen, $C_{1-3}$ alkyl or $C_{1-8}$ acyl; and
n is 1 or 2; the lactam group being trans to the $OR_5$ group.

2. A compound according to claim 1, wherein the other of $R_1$ and $R_2$ is $C_{1-6}$ alkyl-thiocarbonyl, $C_{1-6}$ alkoxy-thiocarbonyl or formyl.

3. A compound according to claim 1, wherein the alkyl moieties of the alkyl-containing groups are methyl or ethyl.

4. A compound according to claim 1, wherein $R_2$ is hydrogen.

5. A compound according to claim 1, wherein $R_3$ and $R_4$ are both methyl or ethyl.

6. A compound according to claim 1, wherein $R_5$ is hydrogen.

7. 6-Formyl-3,4-dihydro-2,2-dimethyl-trans-4-(2-oxo-1-pyrrolidinyl)-2H-benzo[b]pyran-3-ol or 6-formyl-3,4-dihydro-2,2-dimethyl-trans-4-(2-oxo-1-piperidinyl)-2H-benzo[b]pyran-3-ol.

8. 6-Thioacetyl-3,4-dihydro-2,2-dimethyl-trans-4-(2-oxo-1-pyrrolidinyl)-2H-benzo[b]pyran-3-ol; 6-thioacetyl-3,4-dihydro-2,2-dimethyl-trans-4-(2-oxo-1-piperidinyl)-2H-benzo[b]pyran-3-ol; 6-methoxy-thiocarbonyl-3,4-dihydro-2,2-dimethyl-trans-4-(2-oxo-1-pyrrolidinyl)-2H-benzo[b]pyran-3-ol; or 6-methoxy-thiocarbonyl-3,4-dihydro-2,2-dimethyl-trans-4-(2-oxo-1-piperidinyl)-2H-benzo[b]pyran-3-ol.

9. A pharmaceutical composition for treating or preventing hypertension in animals including humans which comprises an anti-hypertensive effective amount of a compound according to claim 1 and a pharmaceutically acceptable carrier.

10. A method of treating or preventing hypertension in animal including humans which comprises administering to the patient an anti-hypertensive effective amount of a compound according to claim 1.

11. A compound of formula (XV):

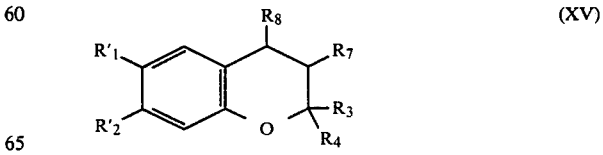

wherein one of the $R_1'$ and $R_2'$ is hydrogen or a group or atom convertible into hydrogen and the other is $C_{1-6}$ alkyl-thiocarbonyl, $C_{1-6}$ alkoxy-thiocarbonyl, $C_{1-6}$ alkyl-thiocarbonyloxy, 1-mercapto $C_{2-7}$ alkyl or formyl or a group or atom convertible thereto, $R_3$ and $R_4$ are as defined in claim 1 and $R_7$ is $OR_5$, in which $R_5$ is as defined in claim 1, and $R_8$ is $-NH(CH_2)_{n+2}COL_1$, $-NH_2$, $-N_3$,

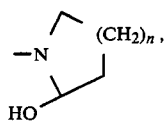

$-HN(CH_2)_{n+2}CH(OR_6)_2$ or $-HNCO(CH_2)_{n+2}L_3$, in which n is as defined in claim 1, $L_1$ is hydroxy or $C_{1-4}$ alkoxy, $L_3$ is chloro, and $R_6$ is $C_{1-4}$ alkyl, or $R_7$ is bromo and $R_8$ is hydroxy, or $R_7$ and $R_8$ together are oxygen; $R_7$, when $OR_5$ or bromo, being trans to $R_8$.

* * * * *